(12) United States Patent
Reed et al.

(10) Patent No.: US 9,861,779 B1
(45) Date of Patent: Jan. 9, 2018

(54) POSITIVE EXPIRATORY PRESSURE DEVICE

(71) Applicants: George Ashford Reed, Lake Oswego, OR (US); Patrick Finn Boileau, Cornelius, OR (US)

(72) Inventors: George Ashford Reed, Lake Oswego, OR (US); Patrick Finn Boileau, Cornelius, OR (US)

( * ) Notice: Subject to any disclaimer, the term of this patent is extended or adjusted under 35 U.S.C. 154(b) by 0 days.

(21) Appl. No.: 15/188,830

(22) Filed: Jun. 21, 2016

(51) Int. Cl.
*A61M 16/00* (2006.01)
*A61M 16/20* (2006.01)
*A61M 39/20* (2006.01)

(52) U.S. Cl.
CPC ........ *A61M 16/20* (2013.01); *A61M 16/0006* (2014.02); *A61M 39/20* (2013.01); *A61M 2039/205* (2013.01); *A61M 2205/0205* (2013.01); *A61M 2205/59* (2013.01)

(58) Field of Classification Search
CPC .............. A61M 16/0006; A61M 16/20; A61M 16/208; A61M 39/10; A61M 39/1011; A61M 39/20; A61M 39/22; A61M 2039/242; A61M 2039/2426; A61M 2039/2433; A61M 2039/2493; A61M 2039/205; A61M 15/0086; A63B 23/18
USPC ................................... D24/110, 110.5, 110.6
See application file for complete search history.

(56) References Cited

U.S. PATENT DOCUMENTS

| | | | | |
|---|---|---|---|---|
| 4,573,460 A * | 3/1986 | Szachowicz | ............... | A61F 2/20 128/200.26 |
| 4,973,047 A * | 11/1990 | Norell | .................... | A63B 23/18 482/13 |
| 5,074,294 A * | 12/1991 | Chiesi | ................ | A61M 15/0086 128/200.14 |
| 5,569,122 A * | 10/1996 | Cegla | ................. | A61M 16/0006 128/200.24 |
| 5,658,221 A * | 8/1997 | Hougen | ............ | A61M 16/0006 482/13 |
| 5,848,588 A * | 12/1998 | Foley | ................. | A61M 15/0086 128/200.14 |
| 8,066,001 B2 * | 11/2011 | Cegla | ............... | A63B 21/00196 128/200.24 |

(Continued)

OTHER PUBLICATIONS

"The RC-Cornet: Information for Families". Great Ormond Street Hospital for Children NHS Trust (Mar. 15, 2010) http://www.curaplex.com/docs/rc_cornet/Curaplex-RC-Cornet-Information-for-families.pdf.*
Promed Oxygen Therapy and Respiratory Support, pp. 1-3 and 11 (Oct. 16, 2013) https://www.thermofisher.com.au/Uploads/file/Healthcare/Medical-Devices-Consumables/Critical-Care/Oxygen-Therapy/promed-Respiratory-New-Product-Catalogue-screen-1373945408-01-RM.pdf.*

*Primary Examiner* — Justine Yu
*Assistant Examiner* — Kathrynn Lyddane
(74) *Attorney, Agent, or Firm* — Mark S Hubert

(57) ABSTRACT

An improved oscillating positive expiratory pressure ("OPEP") device, for respiratory therapy having a self sterilizing flow valve capable of insertion into the curved OPEP body without tools or aids. The flow valve is also tear resistant and incorporates a flared reinforced proximal end. To maximize the benefit to patients, the adjustable therapy selector is constrained from withdrawal and is dimensioned to accept commercially available, standardized respiratory fittings adaptors, mouthpieces and "Tees" that are capable of connection to multiple respiratory therapy devices or medicated aerosol delivery units. The aesthetics have been altered by the addition of an arced handle.

16 Claims, 7 Drawing Sheets

(56) References Cited

U.S. PATENT DOCUMENTS

| | | | |
|---|---|---|---|
| 2007/0042870 A1* | 2/2007 | Bohman | A63B 21/0085 482/11 |
| 2008/0234637 A1* | 9/2008 | McConnell | A61M 5/14216 604/249 |
| 2008/0257355 A1* | 10/2008 | Rao | A61L 2/10 128/207.14 |
| 2009/0199853 A1* | 8/2009 | Cegla | A61M 16/08 128/203.12 |
| 2012/0037155 A1* | 2/2012 | Huang | A61M 16/0816 128/203.12 |
| 2012/0227741 A1* | 9/2012 | Cegla | A63B 21/0088 128/205.12 |
| 2013/0184619 A1* | 7/2013 | Von Hollen | A61M 16/00 601/46 |
| 2014/0276456 A1* | 9/2014 | Eddy | A61L 29/16 604/249 |
| 2016/0045689 A1* | 2/2016 | Cegla | A63B 23/18 128/204.25 |

* cited by examiner

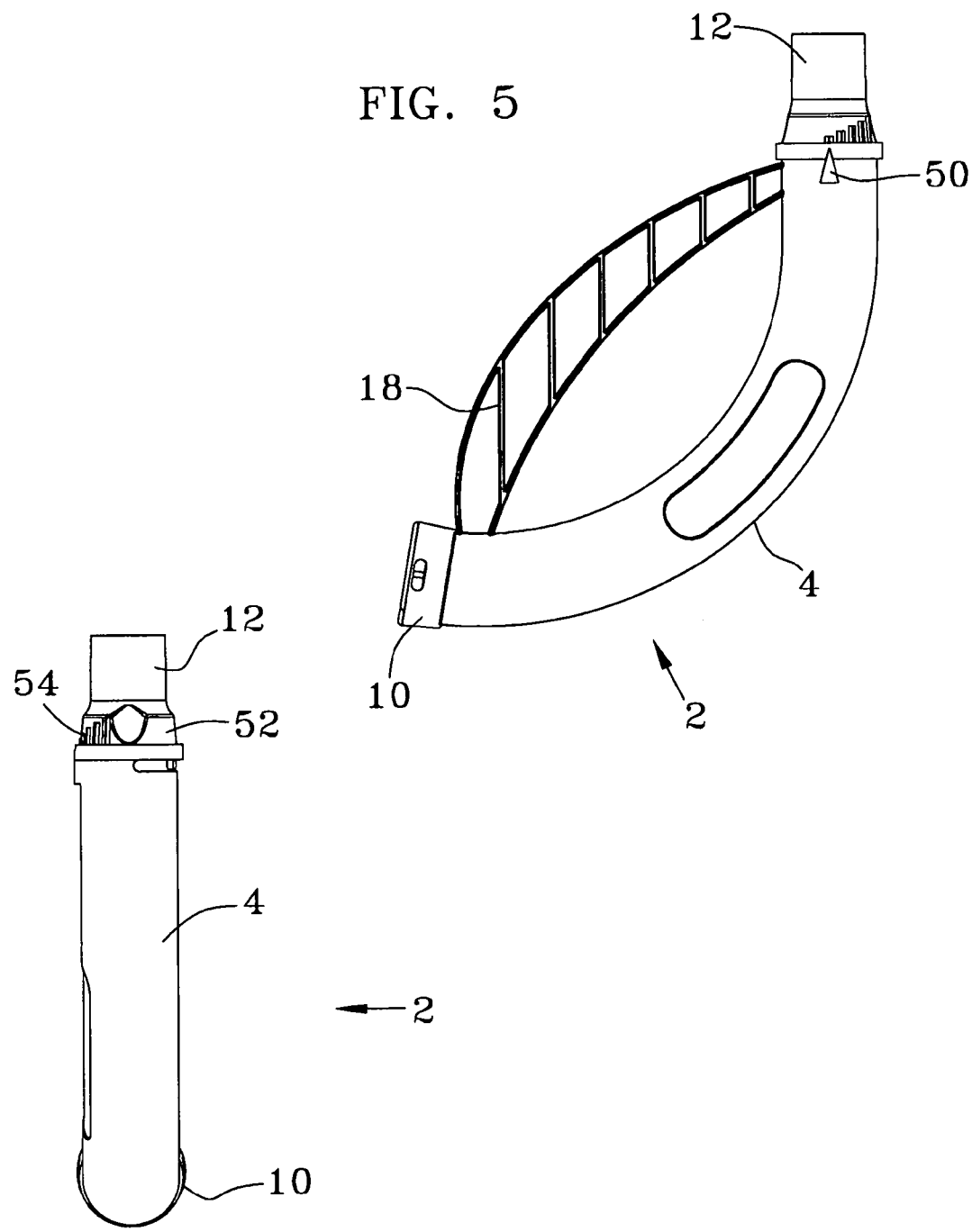

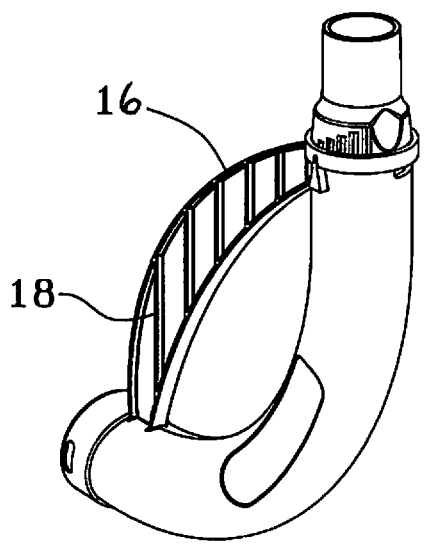
FIG. 11
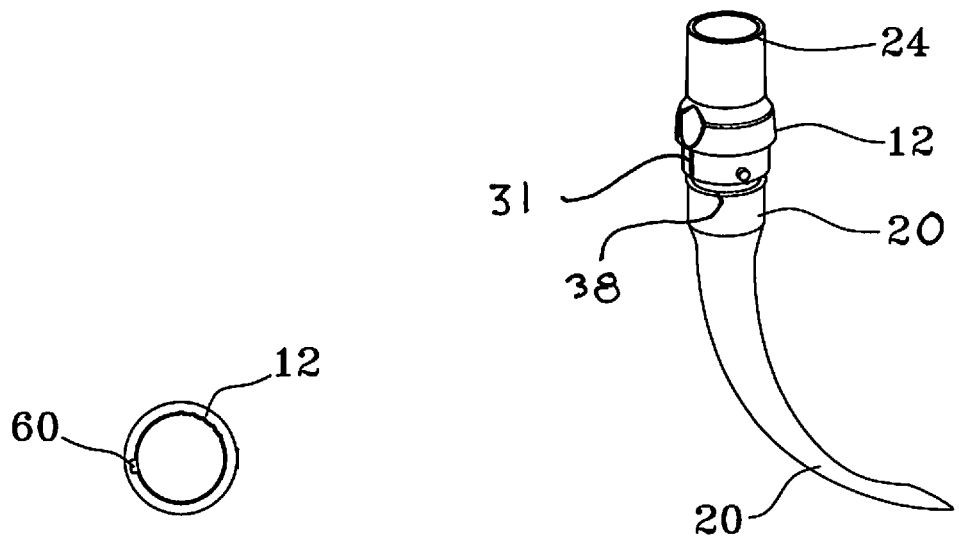
FIG. 12
FIG. 13

US 9,861,779 B1

POSITIVE EXPIRATORY PRESSURE DEVICE

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to medical devices and more particularly to devices for the removal of pulmonary secretions from the lungs of patients undergoing respiratory treatments.

BACKGROUND

When treating patients with respiratory secretions problems, such as Cystic Fibrosis, asthma, COPD and the like, it is advantageous to help clear the patient's lungs of the pulmonary secretions (bronchial mucus) thereon. These can be dislodged best by a series of two different therapies. First, a positive expiratory pressure (PEP) is exerted back into the lungs increasing air pressure into the bronchi and pulmonary alveoli. This pressure prevents airway collapse by stenting the airways, or increasing intrathoracic pressure distal to retained secretions, by collateral ventilation or by increasing functional residual capacity. Second, the gentle application of a series of pressure waves (oscillatory vibrations) additionally provide a percussive effect, reducing the viscoelasticity of the mucus, and dislodging these secretions from the lungs so that they can be expelled (mucocillary clearance).

This can be accomplished with an oscillatory positive expiratory pressure ("OPEP") device that uses the patient's own breathing to generate a series of pressure waves with each exhalation cycle, that causes the thorax to vibrate and loosen the mucus so that it may be expelled.

Prior art OPEP devices, such as the RC-Cornet® Oscillatory PEP Therapy Device utilize a rotating mouthpiece to adjust the frequency and pressure of the oscillations. These therapy selectors are difficult to adjust, do not stay at the set therapy position, and the settings are difficult to visualize. Further, these therapy selectors are not constrained from partial withdrawal from the OPEP body. Partial withdrawal makes the therapy easier on the patient by reducing the amount of exhalation exertion they have to expend, but alters the physical characteristics of the device such that its efficacy is severely diminished. The current devices lack handles and present an undesirable phallic-like aesthetics. The heart of OPEP devices is the silicon polymer flow valve. Being made of medical grade silicone, the flow valve is extremely hard to install and requires its own tool for replacement. The prior art flow valves are completely planar and must be frictionally fit over the distal end of the therapy selector. This is a poor design and lends itself to premature flow valve failure because of splitting and tearing. The prior art devices also require sterilization on a frequent basis.

Henceforth, an improved OPEP device that eliminates all of the prior art downfalls described above would fulfill a long felt need in the respiratory disease treatment industry. This new invention utilizes and combines known and new technologies in a unique and novel configuration to overcome the aforementioned problems and accomplish this.

BRIEF SUMMARY

In accordance with various embodiments, an improved OPEP device, for respiratory therapy is provided.

In one aspect, a OPEP device with a flow valve capable of insertion into the curved OPEP body without tools or aids is provided.

In another aspect, a OPEP device with a tear resistant flow valve incorporating a reinforced proximal end that has been slightly flared, is provided.

In yet another aspect, a OPEP device having a constrained, adjustable therapy selector that is easy to adjust with clear visual and audible indicators and that prevents patients from minimizing the medical benefits of their respiratory therapy is provided.

In yet another aspect, a OPEP device with an easy-remove silicon end cap and an integrated handle is provided.

In yet another aspect, an aesthetically appealing, handled OPEP device that has a vented dust cap and a therapy selector dimensioned to accept commercially available, standardized respiratory fittings adaptors, mouthpieces and "Tees" that are capable of connection to multiple respiratory therapy devices or medicated aerosol delivery units, is provided.

In a final aspect, a OPEP device with a self sterilizing flow valve has been provided.

Various modifications and additions can be made to the embodiments discussed without departing from the scope of the invention. For example, while the embodiments described above refer to particular features, the scope of this invention also includes embodiments having different combination of features and embodiments that do not include all of the above described features.

BRIEF DESCRIPTION OF THE DRAWINGS

A further understanding of the nature and advantages of particular embodiments may be realized by reference to the remaining portions of the specification and the drawings, in which like reference numerals are used to refer to similar components

FIG. 5 is a second side view of the improved OPEP device;

FIG. 6 is a front view of the improved OPEP device;

FIG. 11 is a front perspective view of the OPEP device;

FIG. 12 is a side perspective view of a flow valve affixed to a therapy selector;

FIG. 13 is distal end view of the therapy selector;

DETAILED DESCRIPTION OF CERTAIN EMBODIMENTS

Figure 1:
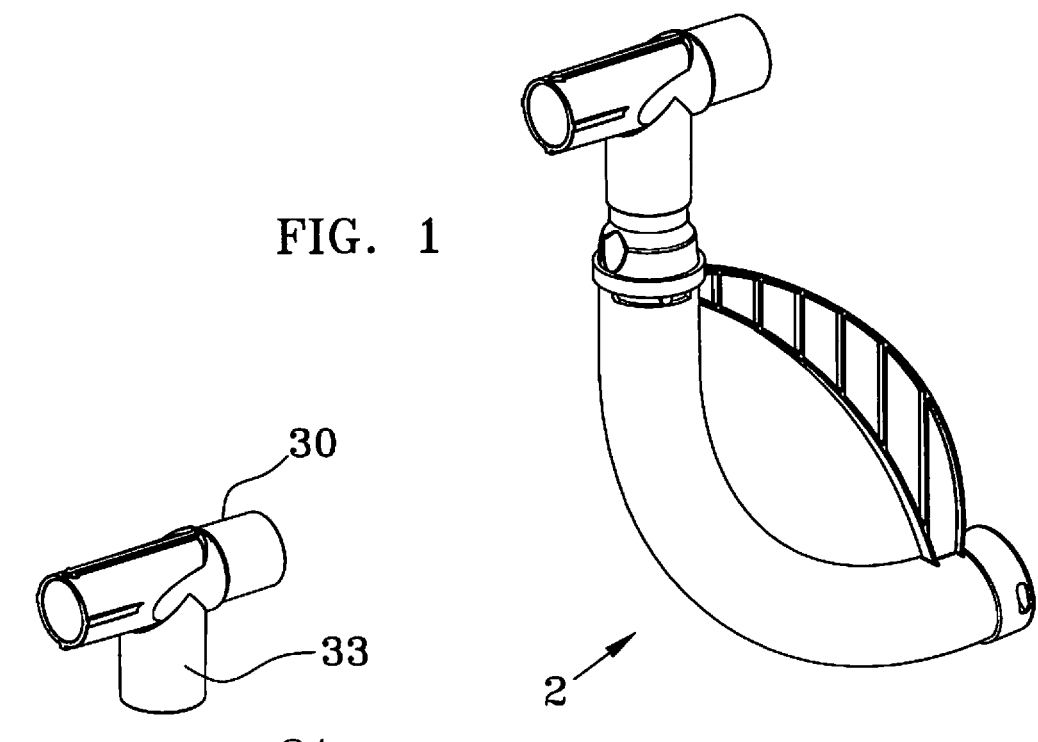
FIG. 1 is a front perspective view of the improved OPEP device with an optional Tee piece installed.

While various aspects and features of certain embodiments have been summarized above, the following detailed description illustrates a few exemplary embodiments in further detail to enable one skilled in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. While various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers herein used to express quantities, dimensions, and so forth, should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

The present invention relates to a novel design for a single patient use improved oscillatory positive exhalation pressure ("OPEP") device that incorporates numerous enhancements over the prior art in both the aesthetics and functionality of the device. It loosens the bronchial mucus for mucocillary clearance through the application of a series of pressure waves. The respiratory therapy with the device 2 is intended to be performed 2-3 times per day for 5 minutes or as recommended by a healthcare provider. Increased intervals and prolonged treatment time may be required in cases of increased breathing difficulty or increased mucus accumulation.

FIGS. 3-8 illustrate that the exterior of the improved OPEP device 2 has a hollow, tubular polymer body 4 having a distal end 6 and a proximal end 8. The length of the body is curved, with the preferred embodiment having an approximate 90 degree curve across the length of it with a tolerance of plus or minus 10 degrees. The overall length of the OPEP body is 9.375 inches plus or minus ½ inch. About the outer perimeter of the distal end a flexible, polymer sound dampening cap 10 is frictionally affixed. In the preferred embodiment this cap 10 is made of silicone. This results in a 14% quieter operation. The cap 10 has a pair of opposed vent orifices 14 formed there through that allow the exhaled air escape from the OPEP body 4. The cap 10 also has a slight groove 80 about the bottom interior periphery that frictionally engages about a raise ring 82 at the distal end of the OPEP body 4. This increases the adherence of the cap 10 to the end of the OPEP body 4. On the bottom inner face of the cap is a set of stiffening ribs 22 (FIG. 2) to retain the circular configuration of the cap as the thickness of the silicone used for construction will not allow the cap to retain its shape under its own mass without the stiffening ribs 22. At the proximal end of the body is rotationally affixed a selectively adjustable therapy selector 12.

Spanning between the distal end 6 and the proximal end 8 of the body 4 is a handle 16. It is directly affixed to the OPEP body 4 at both of it ends. (FIG. 11) The handle is arced and is used as a secure holding apparatus for those with diminished grasping abilities, and it is used to change the visual aesthetics, which many testers have commented has a phallic-like resemblance. The positioning of the handle 16 on the body 4 is not designed to position the device in the correct orientation, as the device is not gravity or position sensitive. It may be used with a patient in any position. The handle 16 has a series of raised ribs 18 to increase its gripability. Not visible in FIGS. 3-6 is a flexible polymer flow valve 20 (FIGS. 12, 14-16) which is frictionally affixed to the therapy selector 12 and resides within the OPEP body 4.

Figure 2:
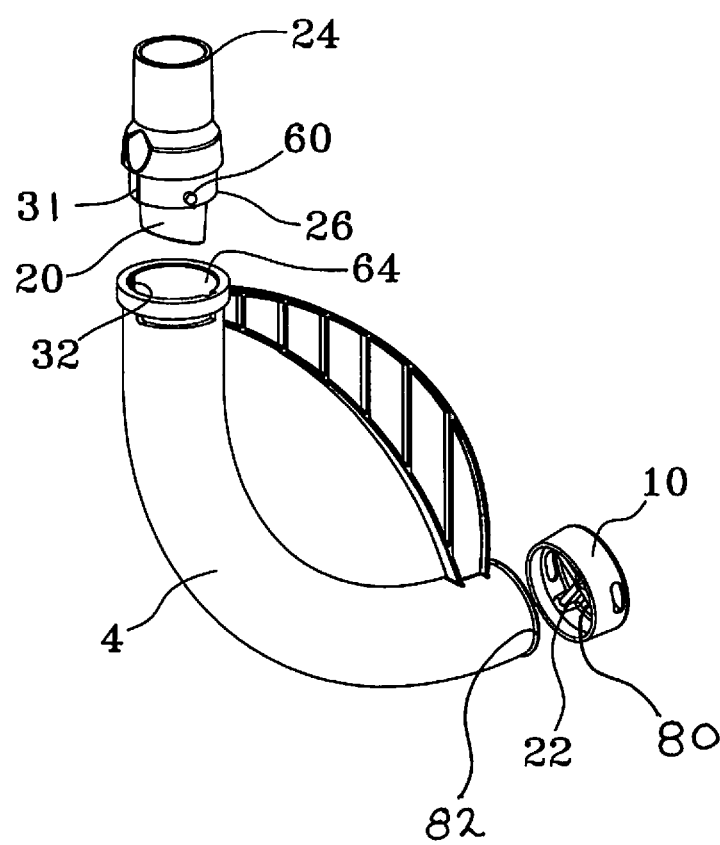
FIG. 2 is a front perspective exploded view of the improved OPEP device with the optional Tee piece.
Figure 3:
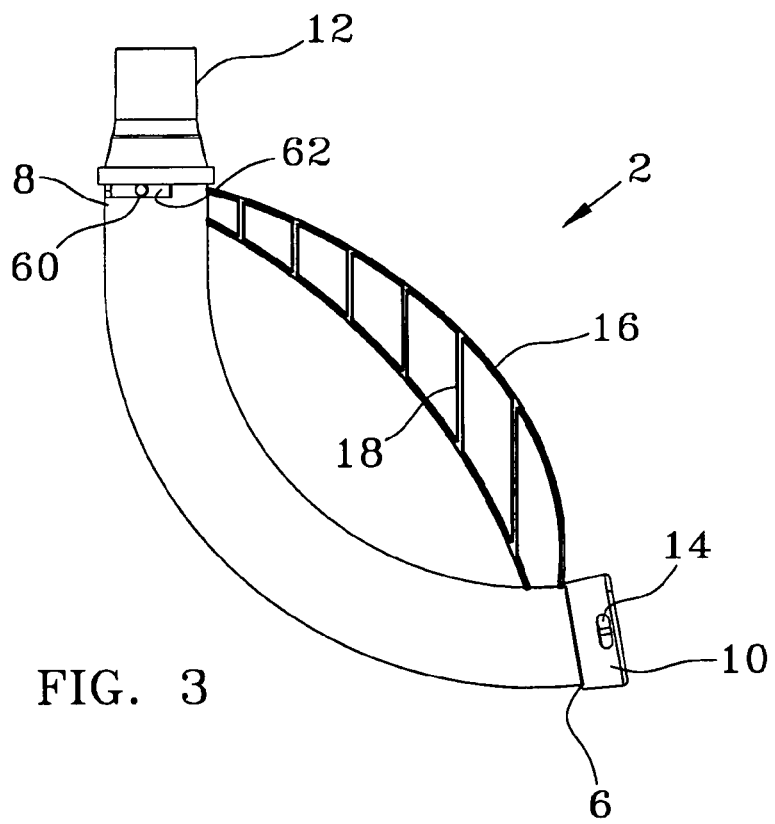
FIG. 3 is a first side view of the improved OPEP device.
Figure 4:
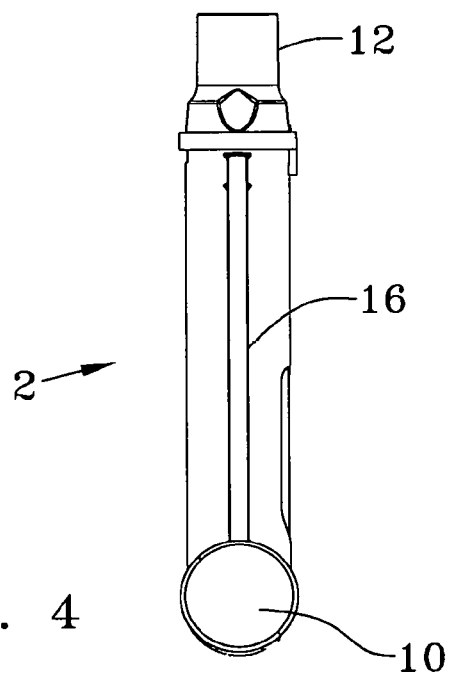
FIG. 4 is a back view of the improved OPEP device.
Figure 7:
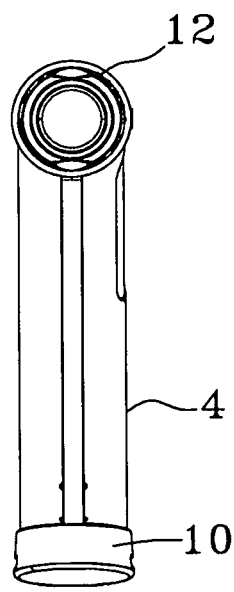
FIG. 7 is a top view of the improved OPEP device.
Figure 8:
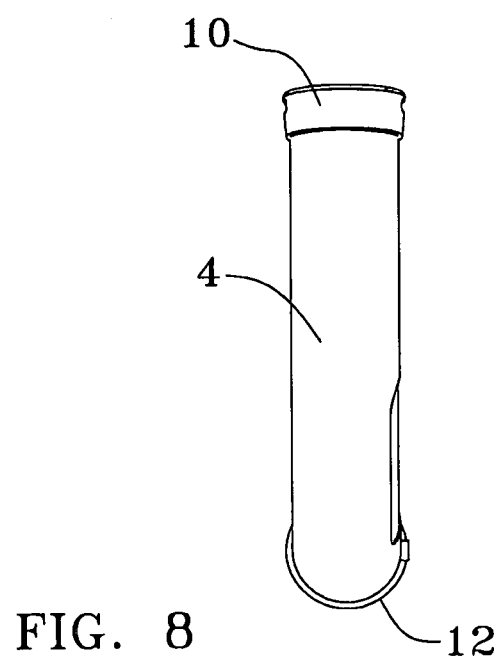
FIG. 8 is a bottom view of the improved OPEP device.

The structure of the improved OPEP device 2 can best be seen with reference to FIGS. 2 and 12. The of the therapy selector 12 is a hollow linear fitting, circular in cross section, having a distal end 26 and a proximal end 24. (FIGS. 2 and 12) The distal end 26 has an outer diameter dimensionally sized to be rotationally and slidingly frictionally received in the opening at the proximal end of the OPEP body 4. The proximal end 24 of the therapy selector 12 has an outer diameter sized to be received in other respiratory adaptors and devices such as a mouthpiece. The proximal end also has an inner diameter sized to receive other respiratory adaptors. Since the medical industry has standardized dimensions for the internal and external connections of the majority of its commercially available devices, these dimensions (generally 18 and 22 mm) are what the preferred embodiment therapy selector is sized to. In FIGS. 1 and 2 the OPEP device is shown coupled to a Tee adaptor 30 which has a 22 mm inner diameter connecting leg 33 that slides over the 22 mm outer diameter of the proximal end of the therapy selector 12. The mouthpiece has an 18 mm outer diameter that engages frictionally with the inner diameter of the proximal end of the therapy selector.

Looking at FIGS. 14-17 one can see that the flow valve 20 is a hollow linear tube made of a polymer, preferably a medical grade silicone. It is replaceable, washable and can be sterilized. The valve 20 has a planar, linear body of two substantially similar, parallel planar strips joined at both their long side edges. It has a proximal end and a distal end, with the proximal end molded into a conical configuration 34, that is self supporting or retains its conical shape when the flow tube is in its relaxed, non attached, non stretched state (As shown in the perspective view of FIG. 16). The flow valve's proximal end terminates in a circular axial cross section. At the proximal tip of the valve 20 is a raised, strengthening ring 38 to resist tears from propagating from the tip of the proximal end when the valve 20 is stretched into place. The inner diameter of the cone is smaller than the outer diameter of the bottom section of the therapy selector such that it can frictionally remain engaged thereon. It has a pair of raised ribs 36 and an arrow embossed on it surface. The ribs 36 help when stretching the cone 34 over the exterior of the bottom section of the therapy selector 12, and the arrow informs the patient which end of the flow valve 20 is to go onto the therapy selector 12.

The flow valve 20 is made to exacting tolerances to fit and work within the OPEP body. The OPEP body has an inside diameter of varying size ranging from one inch to 0.900 inches and a length of approximately nine and 3/8 inches plus or minus 1/2 inch. The flow valve 20 has a width (denoted as X) of 0.886 inches plus or minus 0.25 inches, and a length (denoted as Y) of 5.984 inches plus or minus 1/2 inches. As can be seen, the amount of clearance between the flow valve's sides and the inside wall of the OPEP body may be as large as 1/4 inch is but generally is less that 1/64 of an inch at the narrowest. The wall thickness of the flow valve (denoted as V) is 0.017 inches plus or minus 0.010 inches and the space between the parallel walls (denoted as W) is 0.011 inches plus or minus 0.005 inches. The diameter of the cone 34 is 0.560 inches plus or minus 0.025 inches. On the outer surface of the flow valve 20 is a coating of a lubricating polymer 40. This polymer 40 is not coated onto the interior of the flow valve 20. The polymer 40 allows for the insertion of the flow valve 20 into the OPEP body 4 without any tools. Without the polymer 40, upon insertion, the flow valve 20 will hang up in the inside of the OPEP body 4 both by the friction of its sides against the OPEP body walls and by its planar walls on the bend of the OPEP body 4. This outer, low density polymer coating is any of a variety of poly polymers commonly used as dry film lubricants. These matte coatings may be chemically bonded or physically bonded to the surface. Since they affect both the mass and the durometer of the flow valve 20 which in turn affects the frequency and pressure of the oscillatory pressure wave, they are extremely thin coatings.

In the preferred embodiment any of the family of Parylene® (poly(para-xylylene) polymers), is used here which physically bonds well to medical grade silicone and results in a matte surface that has a very low coefficient of friction with the smooth polymer the OPEP body 4 is made of. This is applied in a vapor deposition tumbling apparatus to a thickness of approximately 0.5 microns with a tolerance of plus or minus 0.2 microns. This coating increases the rubber material hardness of the flow valve 20. The material hardness of the flow valve with the applied coating (including any anti-microbial product) must remain in the 30-40 range of the Type A durometer scale based on the ASTM D2240 standard. If the material hardness is too low, (below 30) the flow valve 20 will not close after a bubble of air has exited and there will not be the generation of a series of pressure pulses. If the material hardness is too high, (over 40) the pressure required to push the air out of the distil edge is too high and the bubble size is too large diminishing the frequency.

In another embodiment a nano sized dry lubricant such as Slick Sil LSR® containing an anti-microbial FluroMed® with silver oxide ions is used. This particular coating combination does not affect the material hardness and is applied chemically. The anti microbial feature eliminated or minimizes the requirement for repeated, regular sterilizations. The problem of accumulated pathogens in the moist environment of the device, is a huge potential liability of using the OPEP device, especially for patients with cystic fibrosis. It is to be noted that the interior of the flow valve will not be coated or treated with a dry lubricant, however it will receive the anti microbial coating.

In a further embodiment, an anti-microbial product may be physically integrated into the fabrication of the silicon such that the flow valve undergoes constant sterilization.

This dry film lubricity allows the rapid insertion and removal of a flow valve 20 without any tools. Without this coating, the flow valve will not install into the OPEP body without a tool. The thickness of the coating onto the flow valve 20 is balanced between its dry lubricity factors and the effect the added weight and material hardness will have on the functionality of the flow valve 20. There are plugs inserted into the ends of the flow valve 20 during the coating process to ensure that no coating gets onto the inside of the flow valve 20 as this would cause an increase in the frequency of the pressure oscillations.

The flow valve 20 is formed by injection molding about a planar "knife" that the flow valve 20 is formed around. To ensure that the thicknesses of the two walls of the valve 20 do not vary considerably from each other, the knife is supported along its length during the molding process by a series of extremely slender pins that contact the knife and stabilize it from sag or droop. In the preferred embodiment the flow valve wall thickness is approximately 0.017 inches plus or minus 0.005 inches. This ensures that the correct pressure oscillations are generated. (The overall effect of a coating increases the frequency of the pressure waves by approximately 1 Hz because of the effect it has on the material hardness) The holes left by the pins in the walls have a negligible effect on the function of the device.

In operation, the flow valve 20 hangs off of the therapy selector 12, with its cone 34 stretched over the bottom section. The flow valve 20 lies in the OPEP body 4 such that one of its parallel walls may lay against inner wall of the OPEP body 4. When the patient exhales through the proximal end of the therapy selector 12, air travels down the flat flow valve 20 but the bend in the flow valve 20 pinches air off into pockets that traverse down the length of the flow valve and exit the distal end. The pressure in the flow valve 20 rises and the flow valve buckles at the bend of the OPEP body 4. When the peak pressure is reached, the distal end of the flow valve opens and these air pockets exit the valve catapulting the end of the flow valve against the wall, releasing its pressure. This process is repeated, providing an oscillation effect at a constant pressure and flow-rate during the entire exhalation phase that is exerted into the patient's lungs as oscillatory positive expiratory pressure "OPEP". This has both a pressure and a frequency that can be adjusted by the twist in the flow valve 20.

When the therapy selector 12 is rotated the indicating arrow shows which operational pressure level has been selected. This twists the flow valve 20 along its length. The flow valve 20 will twist to a helix-like configuration but it will not straighten upon use because of the tolerances involved. The more extreme the helix-like twist in the flow valve along with more of the valve being bent, the larger the bubbles and more tortious the path requiring more exhalation pressure and resulting in a lower frequency of pressure pulses but a higher force of the back pressure wave. Similarly, the straighter and less curved the flow valve 20 the smaller the air bubbles and the less exhaust pressure required with a resultant higher frequency and lower force of back pressure waves.

Since the amount of the flow valve 20 that is bent affects the pressure and frequency, withdrawing the flow valve 20 up the OPEP body 4 by pulling out the bottom section of therapy selector 12 somewhat from the proximal end of the OPEP body 4 will reduce the pressure and the frequency of the oscillatory pulses. This was a huge problem with patients using the device 2 on their own. Since it is hard for some these respiratory patients to perform their therapy at the prescribed therapeutic settings because of the massive amount of bronchial mucus in their lungs, they cheat! They withdraw the therapy selector partially from the OPEP body 4 reducing the effort they have to expel. Unfortunately, this does not provide sufficient oscillatory vibrations for effective mucocillary clearance. Thus, the full benefit of the therapy is lost. This has been countered by a physical barrier to cheating.

The preferred embodiment remedies this situation with a therapy selector withdrawal lock. Extending normally from the bottom section of the therapy selector is a pin 60 that fits into an uninterrupted slot 62 cut into the OPEP body 4 adjacent the proximal end so that pin 60 cannot be removed. (See FIG. 2) This allows the rotation of the therapy selector 12 for the purpose of selecting the desired level of therapy but prevents the withdrawal of the therapy selector 12 from the proximal end of the OPEP body 4.

In a first embodiment the pin 60 (FIGS. 2 and 13) is inserted into the corresponding orifice in the therapy selector 12 after the therapy selector 12 is inserted into the OPEP body 4 and the orifice aligned with the slot 62. (FIG. 3) In an alternate embodiment (FIG. 2) there is a groove 64 running from the proximal end of the OPEP body 4 into the slot 62 (preferably in a perpendicular line) that then allows the insertion of the therapy selector 12 with the pin 60 already installed therein, into the slot 62. The therapy selector withdrawal lock of the preferred embodiment may not be removed without the pin 60 being pushed through the therapy selector, while the alternate embodiment therapy selector withdrawal lock allows the therapy selector to be withdrawn by rotation, but does not allow it to be withdrawn when it is engaged in any one of the therapy selections. With the addition of the anti-microbial additive, removal of the therapy selector to get at the flow valve for sterilization is not necessary, allowing for the use of the first embodiment therapy selector withdrawal lock.

Figure 9:
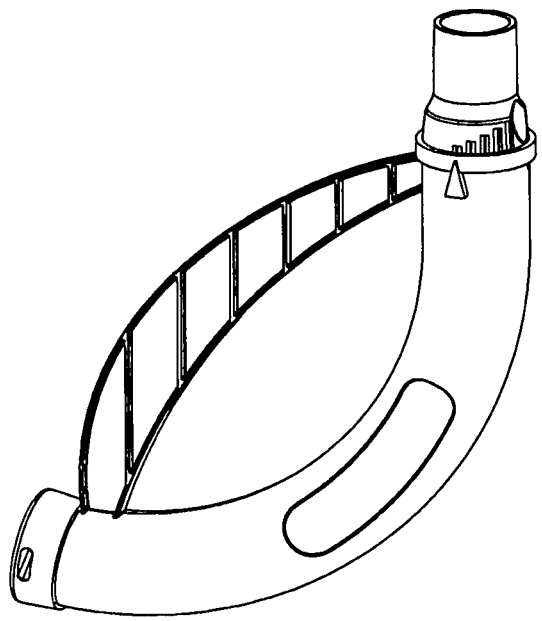
FIG. 9 is a perspective first view of the improved OPEP device with the therapy selector selected to the lowest pressure setting.
Figure 10:
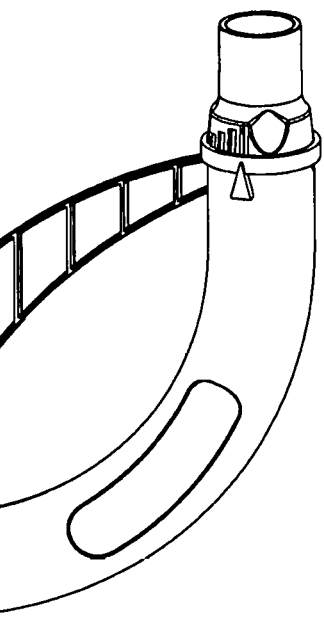
FIG. 10 is a perspective first view of the improved OPEP device with the therapy selector selected to the highest pressure setting.
Figure 14:
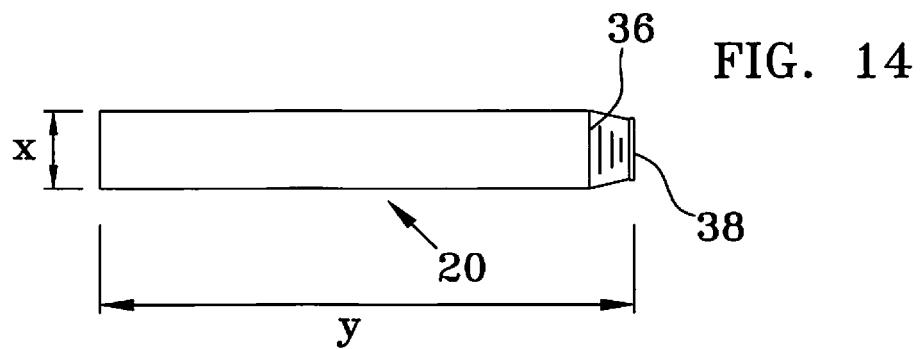
FIG. 14 is a top view of a flow valve.
Figure 15:
FIG. 15 is a cross sectional view of a flow valve.
Figure 16:
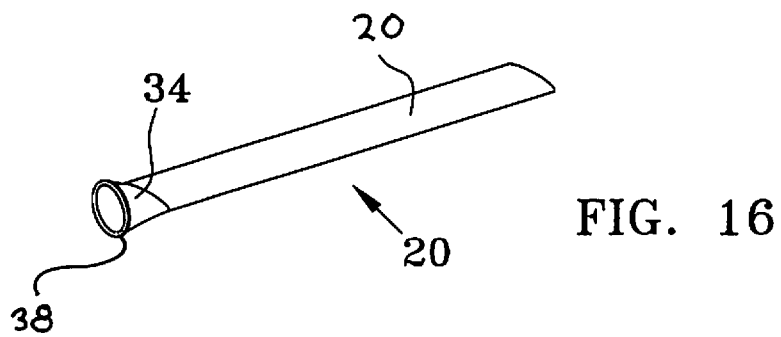
FIG. 16 is a top perspective view of a flow valve.
Figure 17:
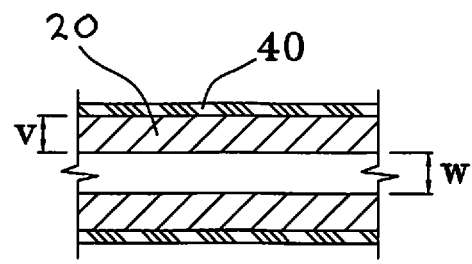
FIG. 17 is an axial cross sectional view of a flow valve.

The therapy selector 12 has a raised linear rib 31 on its outside bottom section that matingly, and rotationally engages any one of a series of slots 32 formed on the inside surface of the proximal end of the OPEP body 4. Rotating the therapy selector to engage the various slots 32 on the OPEP body 4 increases the amount of twist the flow valve experiences inside the OPEP body. This in turn adjusts the pressure and frequency of oscillations. There are a series of different height setting ribs 54 embossed on the outside central section 52 that are spatially aligned with the various slots 32 on the OPEP body 2. There is a highly visible indicating arrow 50 imprinted on the proximal end of the OPEP body that will align with the setting ribs 54 so as to present to the user what operational level of therapy is being performed. FIGS. 9 and 10 show the therapy selector set for the lowest and highest levels of therapy.

The length of the flow valve 20 has been set to approximately six inches (5.984 inches) so as to provide a well gradated series of therapy settings that provide for a lowest setting of only a flat valve that bends in conformance with the radius of the curve in the OPEP body. The remainder of settings have some degree of helical twist along the length of the flow valve. However, the lowest therapy selector setting cannot be bypassed by the patient by partial withdrawal of the therapy selector.

The overall design and structure of the device 2 provides an extremely high level of consistency in the therapy sessions not seen before in any of the prior art devices. The following table sets forth the average pressure, average pressure amplitude and the frequency of pulses for three different fixed flow rates, taken across all therapy settings of the therapy selector. The combination of a flow valve that is fabricated with a wall thickness having a tolerance of 0.010 inches and with the space between parallel walls having a tolerance of 0.005 inches, allows a dry lubricant coating to be placed on the exterior surfaces and still maintain a material hardness between 30 and 40 durometer, so as to allow the following pressure and frequency ranges.

| Parameters | Flow Rate | | |
| --- | --- | --- | --- |
| | 10 lpm | 20 lpm | 40 lpm |
| Ave. Pressure (cmH$_2$O) | 10-13 | 18-21 | 27-41 |
| Ave. Pressure Amplitude (cmH$_2$O) | 7-17 | 22-28 | 51-76 |
| Frequency (Hz) | 8-16 | 12-17 | 19-22 |

Cleaning a non anti-microbial treated OPEP device 2 should be performed every other day and may be accomplished by disassembly and hand washing with a gentle soap. Disinfecting the components of the OPEP device 2 may be accomplished by immersion in boiling water for 10 minutes and air drying thereafter.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture, but instead can be implemented on any suitable hardware, firmware, and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added, and/or subtracted from among other described embodiments, unless the context dictates otherwise. Consequently, although several exemplary embodiments are described above, it will be appreciated that the invention is intended to cover all modifications and equivalents within the scope of the following claims.

Having thus described the invention, what is claimed as new and desired to be secured by Letters Patent is as follows:

1. A respiratory therapy device comprising:
   a curved tubular body having a proximal end and a distal end, said distal end having a raised ring about its exterior perimeter, said tubular body having a 90 degree curve across its length, said curve with a tolerance of plus or minus 10 degrees;

a therapy selector having a first end and a second end, said first end frictionally engageable within said proximal end for rotation, said second end frictionally engageable for connection with standardized 22 mm outside diameter tubing and 18 mm inside diameter tubing;

a flow valve, said flow valve is a hollow linear tube having a material hardness in the range between 30 and 40 durometer as measured by an Type A durometer scale as specified in the ASTM D2240 standard, said flow valve having a top end with a conical configuration, said conical configuration is self-supporting when said flow valve is in a relaxed, non stretched state, and a bottom end, said conical configuration being elastically deformable over said first end of said therapy selector and dimensionally sized for insertion within said tubular body;

a single arced handle affixed to and extending between said proximal end of said tubular body and said distal end of said tubular body; and a cap frictionally engageable about said distal end of said tubular body.

2. The respiratory therapy device of claim 1 wherein said cap has a planar bottom face with a circular side wall extending therefrom, said side wall having a groove about its bottom interior periphery that frictionally engages said raised ring at the distal end of the body, said cap made of a silicon polymer and has a pair of opposing vent orifices formed therethrough said circular side wall.

3. The respiratory therapy device of claim 2 wherein said cap has a set of stiffening ribs formed on an inner side of said bottom face.

4. The respiratory therapy device of claim 1 wherein said flow valve has a planar, linear body of two parallel planar strips joined at both their side edges, said conical configuration at said top end of said flow valve terminating in a circular axial cross section; wherein said planar strips have a thickness of 0.017 inches with a thickness deviation tolerance of plus or minus 0.005 inches.

5. The respiratory therapy device of claim 4 wherein said flow valve has a strengthening ring formed about the top end of the flow valve about the outer perimeter of said conical configuration of said top end of said flow valve.

6. The respiratory therapy device of claim 5 wherein said conical configuration has an inner diameter smaller than an outer diameter of the first end of the therapy selector such that it said conical configuration's surface can frictionally remain engaged thereon, and a pair of raised ribs.

7. The respiratory therapy device of claim 1 wherein said flow valve is coated with an anti-microbial product having silver oxide ions.

8. The respiratory device of claim 7 further comprising a dry lubricant coating having a thickness of 0.5 microns with a thickness tolerance of plus or minus 0.2 microns, said dry lubricant coating affixed to an outer surface of said flow valve, said dry lubricant thickness allowing the flow valve to retain its original range of material hardness in the 30 to 40 durometer range as measured by Type A durometer scale specified in the ASTM D2240 standard.

9. The respiratory therapy device of claim 1 wherein said flow valve is made of a silicon polymer impregnated with an anti-microbial product having silver oxide ions.

10. The respiratory device of claim 9 further comprising a dry lubricant coating having a thickness of 0.5 microns with a thickness tolerance of plus or minus 0.2 microns, said dry lubricant coating affixed to an outer surface of said flow valve, said dry lubricant thickness allowing the flow valve to retain its original range of material hardness in the 30 to 40 durometer range as measured by Type A durometer scale specified in the ASTM D2240 standard.

11. The respiratory device of claim 1 further comprising a dry lubricant coating having a thickness of 0.5 microns with a thickness deviation tolerance of plus or minus 0.2 microns, said dry lubricant coating affixed to an outer surface of said flow valve, said dry lubricant thickness allowing the flow valve to retain its original range of material hardness in the 30 to 40 durometer range as measured by Type A durometer scale specified in the ASTM D2240 standard.

12. The respiratory device of claim 11 wherein said dry lubricant coating is a poly(para-xylyene) polymer and said flow valve has a wall thickness of 0.017 inches with a thickness tolerance of plus or minus 0.005 inches.

13. The respiratory therapy device of claim 1 wherein said therapy selector has a raised linear rib formed on an outside surface of said first end that matingly engages in any one of a series of slots formed on an inside surface of said proximal end of said tubular body, wherein when said therapy selector is rotated, it helically twists said flow valve in said tubular body.

14. The respiratory therapy device of claim 13 wherein said therapy selector has a withdrawal lock, said withdrawal lock comprising a pin that extends normally from said first end of said therapy selector, said pin matingly engagable and irremovably situated in a slot adjacent said proximal end of said tubular body so as to allow the rotation of the therapy selector but prevent any withdrawal of the therapy selector from the proximal end of the tubular body.

15. The respiratory therapy device of claim 13 wherein said therapy selector has a withdrawal lock, said withdrawal lock comprising a pin that extends normally from said first end-of said therapy selector said pin matingly engagable in a closed, uninterrupted slot adjacent said proximal end of said tubular body, said pin engageable in said slot through via a groove formed in a perpendicular line between said slot and the proximal end of said tubular body, so as to allow the rotation of the therapy selector but prevent any withdrawal of the therapy selector from the proximal end of the tubular body.

16. A respiratory therapy device comprising:

a curved tubular body having a proximal end and a distal end;

a therapy selector having a first end and a second end, said first end frictionally engageable within said proximal end of said tubular body for rotation, said second end frictionally engageable for connection with standardized 22-mm outside diameter tubing and 18 mm inside diameter tubing;

a self sterilizing flow valve, said flow valve having a top end formed into a conical configuration with a strengthening ring formed about a tip of the top end, and a bottom end, said top end of said flow valve being elastically deformable over said first end of said therapy selector and said top end of said flow valve dimensionally sized for insertion within said tubular body;

single arced handle affixed to and extending between said proximal and said distal ends of said tubular body; and a cap frictionally engageable about said distal end of said tubular body.

* * * * *